(12) United States Patent
Yang et al.

(10) Patent No.: US 10,246,341 B2
(45) Date of Patent: Apr. 2, 2019

(54) METHOD FOR PRODUCING LITHIUM CARBONATE FROM LOW-LITHIUM BRINE BY SEPARATING MAGNESIUM AND ENRICHING LITHIUM

(71) Applicant: XIANGTAN UNIVERSITY, Xiangtan (CN)

(72) Inventors: Lixin Yang, Xiangtan (CN); Mi Fu, Xiangtan (CN); Yi Wang, Xiangtan (CN); Hongyu Qi, Xiangtan (CN); Yu Xu, Xiangtan (CN); Yali Liu, Xiangtan (CN); Yalin Gui, Xiangtan (CN); Jing He, Xiangtan (CN)

(73) Assignee: XIANGTAN UNIVERSITY, Xiangtan (CN)

( * ) Notice: Subject to any disclaimer, the term of this patent is extended or adjusted under 35 U.S.C. 154(b) by 0 days.

(21) Appl. No.: 15/789,997

(22) Filed: Oct. 21, 2017

(65) Prior Publication Data
US 2018/0044194 A1 Feb. 15, 2018

Related U.S. Application Data

(63) Continuation of application No. PCT/CN2016/091672, filed on Jul. 26, 2016.

(30) Foreign Application Priority Data

Sep. 18, 2015 (CN) .......................... 2015 1 0621200

(51) Int. Cl.
C01D 15/00 (2006.01)
C01D 15/08 (2006.01)
(Continued)

(52) U.S. Cl.
CPC .............. C01D 15/08 (2013.01); B01D 11/04 (2013.01); B01D 12/00 (2013.01); C01F 5/22 (2013.01);
(Continued)

(58) Field of Classification Search
CPC ............ C01D 15/08; C07F 9/11; B01D 12/00
(Continued)

(56) References Cited

FOREIGN PATENT DOCUMENTS

| CN | 105152190 | * 12/2015 |
|---|---|---|
| WO | 2017/045485 | * 3/2017 |

* cited by examiner

Primary Examiner — Steven J Bos
(74) Attorney, Agent, or Firm — Wayne & Ken, LLC; Tony Hom

(57) ABSTRACT

The present invention discloses a method for producing lithium carbonate from a low-lithium brine by separating magnesium and enriching lithium. A salt-lake brine is used as a raw material and is converted into halide salts through dehydration by evaporation and separation by crystallization; the halide salts are directly extracted using trialkyl phosphate or a mixture of trialkyl phosphate and monohydric alcohol, and an organic extraction phase as well as remaining halide salts are obtained after solid-liquid separation; reverse extraction is performed on the organic extraction phase to obtain a lithium-rich solution with a low magnesium-to-lithium ratio, and lithium carbonate is obtained after concentration and removal of magnesium by alkalization. The used solid-liquid extraction method is simple with no co-extraction agent used, and a solute distribution driving force is strong, unaffected by phase equilibrium of the brine extraction agent. The mass ratio of magnesium-to-lithium significantly decreases in the extraction phase.

5 Claims, 1 Drawing Sheet

(51) Int. Cl.
  *B01D 11/04* (2006.01)
  *B01D 12/00* (2006.01)
  *C07F 9/11* (2006.01)
  *C01F 5/22* (2006.01)
  *C01F 5/24* (2006.01)
  C07B 63/00 (2006.01)
(52) U.S. Cl.
  CPC .......................... *C01F 5/24* (2013.01); *C07F 9/11* (2013.01); *C07B 63/00* (2013.01)
(58) Field of Classification Search
  USPC ............................................. 423/179.5, 421
  See application file for complete search history.

METHOD FOR PRODUCING LITHIUM CARBONATE FROM LOW-LITHIUM BRINE BY SEPARATING MAGNESIUM AND ENRICHING LITHIUM

TECHNICAL FIELD

The present invention belongs to inorganic chemistry and generally relates to a production method for extracting lithium from salt-lake brine and specially to a method for producing lithium carbonate from low-lithium brine by separating magnesium and enriching lithium.

BACKGROUND

Lithium in nature mainly exists as spodumene, lepidolite, petalite and the like in a form of pegmatite deposit, salt-lake solution and solid mineral deposit. Extraction of lithium from rock minerals has a high production cost so it has been replaced by extraction from salt-lake brine since 1990s. The brine of salt lake Atacama, salt lake Holmbreto and salt lake Uyuni in a "lithium triangle" area in triple frontier of Chili, Argentina and Bolivia, has a low content in magnesium and provides an excellent resource with low magnesium to lithium ratio. This region has been a primary manufacture location at present due to its simple and economic manufacture technique. While a characteristic of a high magnesium to lithium ratio is shown in lithium-rich lakes located in other regions around the world, such as the US saline lake, the dead sea in west Asia and the salt lake in Qaidam Basin in Qinghai province. Elements lithium and magnesium are located diagonally in the periodical table, presenting similar properties. Separating lithium from a large amount of magnesium salts is rather economically difficult. In reality, technical development of lithium salt industrialization is still in a passive and stagnated condition. Extraction of lithium from salt-lake brine with a high magnesium to lithium ratio has always been a problem unsolved until now and has drawn special attention in scientific and industrial field.

The reserve of lithium salt in salt lake of Qaidam Basin is up to 18 million tons, accounting for 22% of the total lithium reserve in the world. Lithium salt, mainly stored in surface brine, inter-crystal potential water and porous brine in the salt lakes of Qarham, Yiliping, west Taijinair, east Taijinaier and Daqaidam, has an extinguished exploration value as well as a wide application prospect. There are several ways of extracting lithium. Precipitation is suitable for preparing lithium salts from brine with a low magnesium to lithium ratio. While an economic cost is rapidly increasing as long as the mass ratio of magnesium to lithium is over 6, which is unbeneficial to separation of lithium and magnesium. Ion exchange provides solid materials with a selective adsorption on $Li^+$. The properties of some solid materials such as $MnO_2$ nano crystal, $H_{1.6-x}Li_xMn_{1.6}O_4$ lithium ionic sleeve, aluminum hydroxide gel as well as solvent impregnated resins are investigated. However, their lithium adsorption capacities are not large under neutral condition, permeability of adsorbent is bad and solution loss also occurs. Calcination has been applied in preparing lithium carbonate from old brine of west Taijinair salt lake but the energy cost is high and an equipment is corroded seriously. Ionic membrane utilized in electro-osmosis is expensive and the membrane needs to be cleaned and maintained at a regular interval.

Tributyl phosphate and $FeCl_3$ have been utilized respectively as the earliest extraction agent and the earliest co-extraction agent in solvent extraction. As the reverse extraction needs to be carried out in strong acidic condition, no successful industrial production has been reported. In Chinese invention 201210164159.8, Yuan et al., provides a modified method for extracting lithium from lithium-contained brine by multi-stage extraction, using amides and neutral phosphorus-oxygen compounds as an extraction agent, ferric chloride as a co-extraction agent and aliphatic hydrocarbon or aromatic hydrocarbon as a diluting agent. In other invention with a Chinese application no. 201410721174.7, Shidong et al., has recently provided a method for recycling lithium extraction system and for regenerating organic phase by alkali saponification. The present research group adopts $ClO_4^-$ as a co-extract agent in a Chinese application No. 201210143879.6, and extraction is carried out in neutral aqueous solution. However at present, the solvent extraction only limits to liquid-liquid extraction from brine and no breakthrough changes have been achieved in solvent extraction technique.

SUMMARY

The present invention provides a method for producing lithium carbonate from brine by separating magnesium and enriching lithium in an economic and efficient way, in order to solve the existed technical problems mentioned above about separation of lithium from salt-lake brine.

The technical solutions to solving the problems mentioned above in the present invention comprise steps as follows:

1. preparation of halide salts: taking insolation-condensed salt-lake brine with a high magnesium-lithium mass ratio or taking old brine extracted by potassium salt, condensing the brine by heating and evaporation, separating out halide salts containing crystal water; and a water content of the halide salts is 30%~60% in a total mass of the halide salts;

2. solid-liquid extraction: extracting the halide salts by using trialkyl phosphate or a mixture of trialkyl phosphate and monohydric alcohol as an organic phase, and a mass (kg) to volume (L) ratio of a solid-liquid extraction phase is 1.0:(0.5~5.0);

3. solid-liquid separation: filtering a mixture of the solid-liquid extraction, and obtaining an organic extracted phase as well as remaining halide salts after two-phase separation;

4. reverse extraction: reverse extracting the organic extracted phase by using water as a reverse extraction agent; a volume ratio of water to liquid phase is 1.0:(0.5~10.0), and a stage of reverse extraction is 1~5;

5. liquid-liquid separation: still standing a liquid-liquid reverse extracted mixture, separating a water phase after liquid layering, obtaining enriched $Li^+$ solution with a decreased mass ratio of magnesium to lithium, and obtaining a concentrated water phase after reverse extraction by evaporation and concentration;

6. removal of magnesium by alkalization: adding sodium carbonate or sodium hydroxide into the concentrated water phase after reverse extraction, precipitating magnesium carbonate or magnesium hydroxide, controlling pH of a solution to be more than 10, precipitating $Mg^{2+}$ completely, separating by filtration; and 7. preparation of lithium carbonate: adding sodium carbonate into the water phase after the removal of magnesium by alkalization, producing precipitation of the lithium carbonate, filtering, drying and obtaining lithium carbonate product.

The solid-liquid extraction comprises: first extracting the halide salts, heating and melting the remaining halide salts, controlling the water content until the halide salts containing crystal water are separated out, adding trialkyl phosphate or a mixture of trialkyl phosphate and monohydric alcohol in a proportion of 1.0:(0.5~5.0) in a mass volume ratio of solid to liquid, and performing a second stage extraction, and a stage of the solid-liquid extraction is 1~5.

The solid-liquid extraction is in multi-stage cross flow or multi-stage counter flow.

An extraction agent trialkyl phosphate used in the solid-liquid extraction comprises one or more of compounds consisting of: tributyl phosphate, tripentyl phosphate, trihexyl phosphate, tri-n-heptyl phosphate, trioctyl phosphate and isomerides thereof; the monohydric alcohol comprises one or more of compounds consisting of saturated monohydric alcohols with carbon numbers between C6~C20; and a volume ratio of trialkyl phosphate and monohydric alcohol is 1.0: (0.2~4.0).

When a mass ratio of magnesium to lithium is larger than 1.0 in a water phase solution of the reverse extraction, the water phase solution of the reverse extraction is taken as a raw material of the brine in next-stage solid-liquid extraction, and a new separation process for lithium and magnesium to further reduce the magnesium to lithium ratio is taken by preparation of halide salts, solid-liquid extraction, solid-liquid separation, reverse extraction and liquid-liquid separation from the step a to the step e.

The extraction agent trialkyl phosphate or the mixture of the trialkyl phosphate and the monohydric alcohol is reused after reverse extraction and liquid-liquid separation.

The raw material brine is provided from different kinds of lithium contained salt-lake brine, underground brine, oil field brine, well brine or a condensing solution of seawater after salt preparation.

Compared with the prior art, the present invention changes brine into halide salts, and changes liquid-liquid extraction into solid-liquid extraction. Trialkyl phosphate or a mixture of trialkyl phosphate and monohydric alcohol is provided as the extraction agent to extract lithium from halide salts and solubilization as well as selectivity of micro emulsion to metal ions are utilized to perform the separation of magnesium and lithium, achieving unexpected results. A new approach is provided for the present exploration of lithium resource from salt-lake brine with a high magnesium to lithium ratio. The present invention has the following advantages.

1. The chemistry-industry involved unit is simple to operate using solid-liquid extraction of halide salts of salt lake, since no calcination on halide salts is demanded before extraction, and processes are easy to realize. This method is especially suitable for decreasing a magnesium to lithium ratio from salt-lake brine in which a magnesium to lithium mass ratio is lower than 120 and obtaining lithium enriched solution, which meets the requirement for producing lithium salts to produce lithium carbonate.

2. Compared to the liquid-liquid extraction, the solid-liquid extraction utilized in the present method provides a great distribution driving force on solute, and is unaffected by a two-phase equilibrium of the extraction agent for brine. No co-extraction agent is demanded, and an extraction ability is significantly enhanced by a direct extraction from halide salts using trialkyl phosphate or a mixture of trialkyl phosphate and monohydric alcohol. A $Li^+$ extraction rate higher than 90% as well as a decreased magnesium to lithium ratio by several times is achieved by multi-stage repeated processes consisting of: extraction of halide salts, dissolving after separation and separating halide salts out.

3. A high emergence rate of metal ions is achieved by using water for a reverse extraction of organic phase as the density difference between two phases is great and a phase separation is simple. The extraction rate of $Li^+$ and $Mg^{2+}$ are both higher than 90%. A direct and recycled use of trialkyl phosphate or a mixture of trialkyl phosphate and monohydric alcohol, completely overcomes the difficulties in simultaneous cycling and in simultaneous reusing of an extraction agent, a co-extraction agent and a diluting agent in liquid-liquid extraction.

4. The extraction agent trialkyl phosphate or a mixture of trialkyl phosphate and monohydric alcohol is universal and easy to obtain; wherein the length of an alkyl group imposes a significant influence on the solubility of an extraction agent in water as well as on the solubility of water in organic phase. Regulating a molecule structure is able to decrease a solubility loss of the extraction agent and further increase an ability thereof in magnesium/lithium separation. The extraction properties of trialkyl phosphate or a mixture of trialkyl phosphate and monohydric alcohol is unaffected by a pH value in brine and extraction can be carried out in neutral or weak acidic conditions. The solid-liquid extraction intensifies solubility of halide salts in the organic phase as well as spherical structure formation of micro emulsion, and is beneficial to enriching lithium and separating $Li^+$ from $Mg^{2+}$. The said type of extraction agents provides a low toxicity and can be degraded naturally, imposing a weakly negative effect on environmental protection of salt lakes.

DETAILED DESCRIPTION

Figure 1:
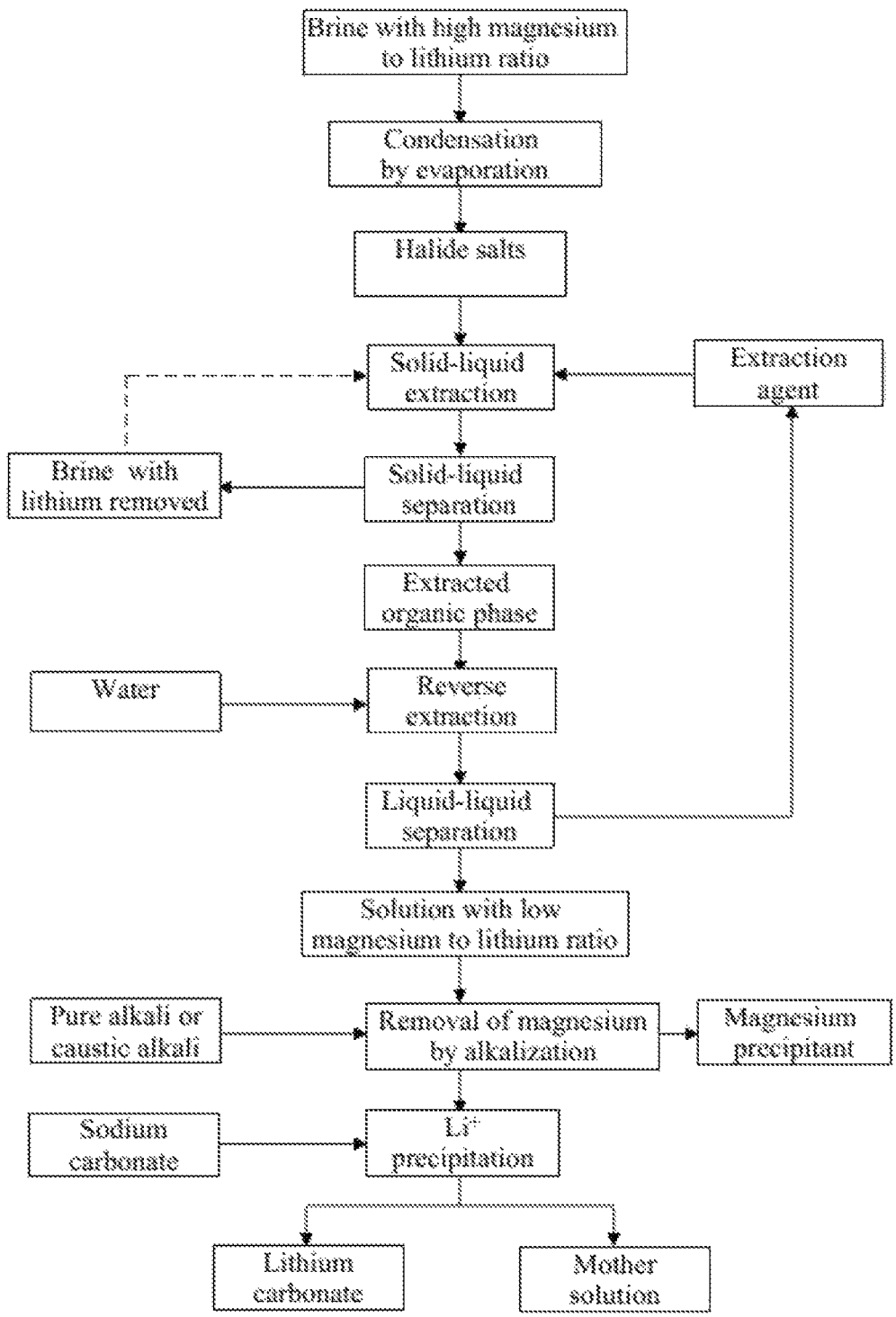
FIG. 1 shows a process flow diagram of producing lithium carbonate from low-lithium brine by separating magnesium and enriching lithium in present invention.

A further description of the present invention is provided with embodiments as follows.

Embodiment 1

The content of $Li^+$, $Mg^{2+}$ and $SO_4^{2+}$ are respectively 2.24 g/L, 118.00 g/L, 39.87 g/L and a magnesium to lithium ratio is equivalent to 52.58 in old brine in a salt lake located in Qaidam Basin of Qinghai province. 350 mL of the old brine was taken into a 1000 mL beaker and was heated for condensation above a temperature adjustable furnace. Water was evaporated, which accounted for 25% of total mass of the brine, and the solution were changed into hydrated halide salts after cooling. The salts were transferred into a mechanical mixing vessel, and 334.5 mL of trihexyl phosphate was added to achieve a mass volume ratio equivalent to 1:1 (g/mL). Solid-liquid extraction was carried out for 30 mins under room temperature. Then solid liquid mixtures were transferred in a sand core funnel and vacuum filtration was carried out, and the extracted organic-phase filtrate and remaining halide salts were obtained. The remaining halide salts were heated and melted to completion. Then the melted halide salts were cooled and completely separated out. Hydrated halide salts were obtained for the second time. Multiple stage extraction: $2^{nd}$ stage, $3^{rd}$ stage and $4^{th}$ stage extractions were successively carried out in a cross-flow manner according to the operation requirements of the first time.

The concentrations of $Li^+$ and $Mg^{2+}$ during the extraction process were sampled and analyzed respectively by a Japanese Shimadzu atomic absorption spectrophotometer AA-7000 and an EDTA titrimetric volumetry. The results are shown in table. 1.

Table. 1 results of four stage solid liquid cross-flow extraction by trihexyl phosphate from an old brine with a magnesium to lithium mass ratio of 52.6 in a salt lake located in Qinghai province

TABLE 1 results of four stage solid liquid cross-flow extraction by trihexyl phosphate from an old brine with a magnesium to lithium mass ratio of 52.6 in a salt lake located in Qinghai province

| Stage of extraction | $E(Li^+)/\%^a$ | | $E(Mg^{2+})/\%^b$ | | $m_o(Mg^{2+})/m_o(Li^+)^c$ | | $m_s(Mg^{2+})/m_s(Li^+)^d$ |
|---|---|---|---|---|---|---|---|
| | Single stage | Accumulative | Single stage | Accumulative stages | Single stage | Accumulative stages | |
| 1 | 21.91 | 21.91 | 4.75 | 4.75 | 11.40 | 11.40 | 64.14 |
| 2 | 23.45 | 40.22 | 4.77 | 9.30 | 13.05 | 12.15 | 79.79 |
| 3 | 25.71 | 55.59 | 4.83 | 13.67 | 14.98 | 12.93 | 102.21 |
| 4 | 27.03 | 67.59 | 4.86 | 17.87 | 18.36 | 13.90 | 133.28 | wherein,
[a] stands for extraction rate of $Li^+$;
[b] stands for extraction rate of $Mg^{2+}$;
[c] stands for mass ratio of magnesium to lithium in organic phase;
[d] stands for mass ratio of magnesium to lithium in the remaining halide salts..
The meaning of symbol is the same in following tables.

The extracted phases from four stages were merged and organic extraction phase and water were respectively added in a separating funnel with a phase ratio of organic phase to water $V_o/V_w$ equivalent to 1:1 and reverse extraction was carried out. The mixtures were vibrated for 30 mins repeatedly in a temperature-constant cooling water bath SHA-2A at 20° C. and at a speed of 200 r/min. The solutions were then placed still for 30 mins and a reverse extracted water phase was finally obtained after phase separation, with a decreased magnesium to lithium ratio. Samples were analyzed and results showed that reverse extraction rate of $Li^+$ is up to 80.3%; reverse extraction rate of $Mg^{2+}$ was 56.0%; and a mass ratio magnesium to lithium declined to 9.7 in the reserve extracted water phase. In the concentrated reverse extracted solution with a low magnesium to lithium ratio, sodium carbonate solution was added to remove majority of $Mg^{2+}$, then sodium hydroxide was again added into the solution after separation, to completely precipitate magnesium. Solution of sodium carbonate was added into the filtered solution to form precipitation, and separation and desiccation were carried out to obtain a lithium carbonate product.

Embodiment 2

350 mL of the old brine in embodiment 1 was taken into a 1000 mL beaker, in which 11.49 g of $LiCl.H_2O$ with its purity analyzed as 97% was added. The mass ratio of magnesium to lithium in the mixture was equal to 20.00. The solution was heated for condensation above a temperature adjustable furnace. Water was evaporated, which accounted for 25% of total mass of the starting brine, and the solution were changed into hydrated halide salts after cooling. The salts were transferred into a mechanical mixing vessel, and 366.8 mL of trihexyl phosphate was added to achieve a mass volume ratio equivalent to 1:1 (g/mL). Solid-liquid extraction was carried out for 30 mins under room temperature. Then solid liquid mixtures were transferred in a sand core funnel and vacuum filtration was carried out, and the extracted organic-phase filtrate and remaining halide salts were obtained. The remaining halide salts were heated and melted to completion. Then the melted halide salts were cooled and separated out. Hydrated halide salts were obtained for the second time. Multiple stage extraction: $2^{nd}$ stage, $3^{rd}$ stage and $4^{th}$ stage extractions were successively carried out in a cross flow according to the operation requirements of the first time.

The concentrations of $Li^+$ and $Mg^{2+}$ during the extraction process were sampled and analyzed. The results are shown in table. 2.

Table. 2 results of four stage solid liquid cross-flow extraction by tributyl phosphate from an old brine with a magnesium to lithium mass ratio of 20.0 in a salt lake located in Qinghai province

TABLE 2 results of four stage solid liquid cross-flow extraction by tributyl phosphate from an old brine with a magnesium to lithium mass ratio of 20.0 in a salt lake located in Qinghai province

| Stage of extraction | $E(Li^+)/\%$ | | $E(Mg^{2+})/\%$ | | $m_o(Mg^{2+})/m_o(Li^+)$ | | $m_s(Mg^{2+})/m_s(Li^+)$ |
|---|---|---|---|---|---|---|---|
| | Single stage | Accumulative stages | Single stage | Accumulative stages | Single stage | Accumulative stages | |
| 1 | 18.00 | 18.00 | 5.31 | 5.31 | 5.90 | 5.90 | 23.09 |
| 2 | 19.64 | 34.11 | 5.10 | 10.14 | 6.00 | 5.95 | 27.26 |
| 3 | 22.34 | 48.83 | 5.16 | 14.78 | 6.30 | 6.05 | 33.29 |
| 4 | 25.13 | 61.69 | 4.94 | 19.00 | 6.55 | 6.16 | 42.27 |

The extracted phases from four stages were merged and organic extraction phase and water were respectively added in a separating funnel with a phase ratio of organic phase to water $V_o/V_w$ equivalent to 1:1 and reverse extraction was carried out. The mixtures were vibrated for 30 mins repeatedly in a temperature-constant cooling water bath SHA-2A at 20° C. and at a speed of 200 r/min. The solutions were then placed still for 30 mins and a reverse extracted water phase was finally obtained after phase separation, with a decreased magnesium to lithium ratio. Samples were analyzed and results showed that reverse extraction rate of $Li^+$ was up to 81.5%; reverse extraction rate of $Mg^{2+}$ was 55.1%; and a mass ratio magnesium to lithium declined to 4.2 in the reserve extracted water phase. In the concentrated reverse extracted solution with a low magnesium to lithium ratio, sodium carbonate solution was added to remove majority of $Mg^{2+}$, then sodium hydroxide was again added into the solution after separation, to completely precipitate magnesium. Solution of sodium carbonate was added into the filtered solution to form precipitation, and separation and desiccation were carried out to obtain a lithium carbonate product.

Embodiment 3

350 mL of the old brine in embodiment 1 was taken into a 1000 mL beaker and the mass ratio of magnesium to lithium in the mixture was equal to 52.58. The brine was heated for condensation above a temperature adjustable furnace. Water was evaporated, which accounted for 25% of total mass of the brine, and the solution were changed into hydrated halide salts after cooling. The salts were transferred into a mechanical mixing vessel, and 354.7 mL of tributyl phosphate was added to achieve a mass to volume ratio equivalent to 1:1 (g/mL). Solid-liquid extraction was carried out for 30 mins under room temperature. Then solid liquid mixtures were transferred in a sand core funnel and vacuum filtration was carried out, and the extracted organic-phase filtrate and remaining halide salts were obtained. The remaining halide salts were heated and melted to completion. Then the melted halide salts were cooled and separated out. Hydrated halide salts were obtained for the second time. Multiple stage extraction: $2^{nd}$ stage, $3^{rd}$ stage and $4^{th}$ stage extractions were successively carried out in a cross flow according to the operation requirements of the first time.

The concentrations of $Li^+$ and $Mg^{2+}$ during the extraction process were sampled and analyzed. The results are shown in table. 3.

Table. 3 results of four stage solid liquid cross-flow extraction by trihexyl phosphate from an old brine with a magnesium to lithium mass ratio of 52.6 in a salt lake located in Qinghai province

TABLE 3 results of four stage solid liquid cross-flow extraction by trihexyl phosphate from an old brine with a magnesium to lithium mass ratio of 52.6 in a salt lake located in Qinghai province

| | $E(Li^+)/\%$ | | $E(Mg^{2+})/\%$ | | $m_o(Mg^{2+})/m_o(Li^+)$ | | |
|---|---|---|---|---|---|---|---|
| Stage of extraction | Single stage | Accumulative stages | Single stage | Accumulative stages | Single stage | Accumulative stages | $m_s(Mg^{2+})/m_s(Li^+)$ |
| 1 | 47.21 | 47.21 | 16.26 | 16.26 | 18.11 | 18.11 | 83.41 |
| 2 | 49.26 | 73.22 | 15.90 | 29.58 | 26.92 | 21.24 | 138.26 |
| 3 | 56.17 | 88.26 | 15.29 | 40.34 | 37.62 | 24.04 | 267.24 |
| 4 | 59.17 | 95.21 | 14.88 | 49.22 | 67.20 | 27.18 | 557.18 |

The extracted phases from four stages were merged and organic extraction phase and water were respectively added in a separating funnel with a phase ratio of organic phase to water $V_o/V_w$ equivalent to 1:1 and reverse extraction was carried out. The mixtures were vibrated for 30 mins repeatedly in a temperature-constant cooling water bath SHA-2A at 20° C. and at a speed of 200 r/min. The solutions were then placed still for 30 mins and a reverse extracted water phase was finally obtained after phase separation, with a decreased magnesium to lithium ratio. Samples were analyzed and results showed that reverse extraction rate of $Li^+$ was up to 94.1%; reverse extraction rate of $Mg^{2+}$ was 93.1%; and a mass ratio magnesium to lithium declined to 26.8 in the reserve extracted water phase. Condensation was carried out in the reverse extracted water phase. A new separation process for lithium and magnesium was taken by preparation of halide salts, solid-liquid extraction, solid-liquid separation, reverse extraction and liquid-liquid separation, until the magnesium to lithium ratio declined below 10. Sodium carbonate solution was added to remove majority of $Mg^{2+}$ in the concentrated reverse extracted solution with a low magnesium to lithium ratio, then sodium hydroxide was again added into the solution after separation, to completely precipitate magnesium. Solution of sodium carbonate was added into the filtered solution to form precipitation, and separation and desiccation were carried out to obtain a lithium carbonate product.

Embodiment 4

350 mL of the old brine in embodiment 1 was taken into a 1000 mL beaker, in which 11.52 g of $LiCl\cdot H_2O$ with its purity analyzed of 97% was added. The mass ratio of magnesium to lithium in the mixture was equal to 19.97. The solution was heated for condensation above a temperature adjustable furnace. Water was evaporated, which accounted for 25% of total mass of the starting brine, and the solution were changed into hydrated halide salts after cooling. The salts were transferred into a mechanical mixing vessel, and 366.1 mL of tributyl phosphate was added to achieve a mass to volume ratio equivalent to 1:1 (g/mL). Solid-liquid extraction was carried out for 30 mins under room temperature. Then solid liquid mixtures were transferred in a sand core funnel and vacuum filtration was carried out, and the extracted organic-phase filtrate and remaining halide salts were obtained. The remaining halide salts were heated and melted to completion. Then the melted halide salts were cooled and separated out. Hydrated halide salts were obtained for the second time. Multiple stage extraction: $2^{nd}$ stage, $3^{rd}$ stage and $4^{th}$ stage extractions were successively carried out in a cross flow according to the operation requirements of the first time.

The concentrations of $Li^+$ and $Mg^{2+}$ during the extraction process were sampled and analyzed. The results are shown in table. 4.

Table. 4 results of four stage solid liquid cross-flow extraction by tributyl phosphate from an old brine with a magnesium to lithium mass ratio of 20.0 in a salt lake located in Qinghai province

TABLE 4 results of four stage solid liquid cross-flow extraction by tributyl phosphate from an old brine with a magnesium to lithium mass ratio of 20.0 in a salt lake located in Qinghai province

| Stage of extraction | $E(Li^+)/\%$ | | $E(Mg^{2+})/\%$ | | $m_o(Mg^{2+})/m_o(Li^+)$ | | $m_s(Mg^{2+})/m_s(Li^+)$ |
|---|---|---|---|---|---|---|---|
| | Single stage | Accumulative stages | Single stage | Accumulative | Single stage | Accumulative stages | |
| 1 | 40.07 | 40.07 | 16.01 | 16.01 | 7.97 | 7.97 | 27.97 |
| 2 | 43.14 | 65.92 | 16.02 | 29.47 | 10.39 | 8.92 | 41.31 |
| 3 | 44.35 | 81.03 | 15.75 | 40.57 | 14.67 | 9.99 | 62.54 |
| 4 | 44.99 | 89.57 | 15.83 | 49.98 | 22.00 | 11.14 | 95.69 |

The extracted phases from four stages were merged and organic extraction phase and water were respectively added in a separating funnel with a phase ratio of organic phase to water $V_o/V_w$ equivalent to 1:1 and reverse extraction was carried out. The mixtures were vibrated for 30 mins repeatedly in a temperature-constant cooling water bath SHA-2A at 20° C. and at a speed of 200 r/min. The solutions were then placed still for 30 mins and a reverse extracted water phase was finally obtained after phase separation, with a decreased magnesium to lithium ratio. Samples were analyzed and results showed that reverse extraction rate of $Li^+$ was up to 94.7%; reverse extraction rate of $Mg^{2+}$ was 92.6%; and a mass ratio magnesium to lithium declined to 10.9 in the reserve extracted water phase. In the concentrated reverse extracted solution with a low magnesium to lithium ratio, sodium carbonate solution was added to remove majority of $Mg^{2+}$, then sodium hydroxide was again added into the solution after separation, to completely precipitate magnesium. Solution of sodium carbonate was added into the filtered solution to form precipitation, and separation and desiccation were carried out to obtain a lithium carbonate product.

Embodiment 5

20 mL of the old brine in embodiment 1 was taken into a 100 mL beaker and the mass ratio of magnesium to lithium was equal to 52.58. The brine was heated for condensation above a temperature adjustable furnace. Water was evaporated, which accounts for 25% of total mass of the brine, and the solution were changed into hydrated halide salts after cooling. The salts was transferred into a mechanical mixing vessel, and 20 mL of tributyl phosphate as well as 20 mL of 2-ethylhexanol were added to achieve a mass to volume ratio equivalent to 1:2 (g/mL). Solid-liquid extraction was carried out for 30 mins under room temperature. Then solid liquid mixtures were transferred in a sand core funnel and vacuum filtration was carried out, obtaining the extracted organic-phase filtrate and remaining halide salts. The remaining halide salts were dissolved in water and fix its volume to 1000 mL in a volumetric flask. Samples were taken to analyze the concentration of $Li^+$ and $Mg^{2+}$ thereof. The results showed that a extraction rate of $Li^+$ is 50.2%; a extraction rate of $Mg^{2+}$ is 4.1% and a mass ratio of magnesium to lithium is 4.3 in the organic extracted phase.

The extracted phases from four stages are merged and organic extraction phase and water were respectively added in a separating funnel with a phase ratio of organic phase to water $V_o/V_w$ equivalent to 2:1 and reverse extraction was carried out. The mixtures were vibrated for 30 mins repeatedly in a temperature-constant cooling water bath SHA-2A at 20° C. and at a speed of 200 r/min. The solutions were then placed still for 30 mins and a reverse extracted water phase was finally obtained after phase separation, with a decreased magnesium to lithium ratio. Samples were analyzed and results showed that reverse extraction rate of $Li^+$ is up to 96.5%; reverse extraction rate of $Mg^{2+}$ is 87.2% and a mass ratio magnesium to lithium declined to 3.9 in the reserve extracted water phase. In the concentrated reverse extracted solution with a low magnesium to lithium ratio, sodium carbonate solution was added to remove majority of $Mg^{2+}$, then sodium hydroxide was again added into the solution after separation, to completely precipitate magnesium. Solution of sodium carbonate was added into the filtered solution to form precipitation, and separation and desiccation were carried out to obtain a lithium carbonate product.

Embodiment 6

20 mL of the old brine in embodiment 1 was taken into a 100 mL beaker and the mass ratio of magnesium to lithium in the mixture was equal to 52.58. The brine was heated for condensation above a temperature adjustable furnace. Water was evaporated, which accounted for 25% of total mass of the brine, and the solution were changed into hydrated halide salts after cooling. The salts were transferred into a mechanical mixing vessel, and 20 mL of tributyl phosphate as well as 20 mL of dl-2-octanol were added to achieve a mass to volume ratio equivalent to 1:2 (g/mL).

Solid-liquid extraction was carried out for 30 mins under room temperature. Then solid liquid mixtures were transferred in a sand core funnel and vacuum filtration was carried out, and the extracted organic-phase filtrate and remaining halide salts were obtained. The remaining halide salts were dissolved in water and fix its volume to 1000 mL in a volumetric flask. Samples were taken to analyze the concentration of $Li^+$ and $Mg^{2+}$ thereof. The results showed that a extraction rate of $Li^+$ was 32.4%; a extraction rate of $Mg^{2+}$ was 4.6% and a mass ratio of magnesium to lithium was 7.4 in the organic extracted phase.

The extracted phases from four stages were merged and organic extraction phase and water were respectively added in a separating funnel with a phase ratio of organic phase to water $V_o/V_w$ equivalent to 2:1 and reverse extraction was carried out. The mixtures were vibrated for 30 mins repeatedly in a temperature-constant cooling water bath SHA-2A at 20° C. and at a speed of 200 r/min. The solutions w then placed still for 30 mins and a reverse extracted water phase was finally obtained after phase separation, with a decreased magnesium to lithium ratio. Samples were analyzed and results showed that reverse extraction rate of $Li^+$ was up to 91.6%; reverse extraction rate of $Mg^{2+}$ was 87.6%; and a mass ratio magnesium to lithium declined to 7.1 in the reserve extracted water phase. In the concentrated reverse extracted solution with a low magnesium to lithium ratio, sodium carbonate solution was added to remove majority of $Mg^{2+}$, then sodium hydroxide was again added into the solution after separation, to completely precipitate magnesium. Solution of sodium carbonate was added into the filtered solution to form precipitation, and separation and desiccation were carried out to obtain a lithium carbonate product.

Embodiment 7

The concentration of $Li^+$, $Mg^{2+}$ and $SO_4^{2+}$ were respectively 0.87 g/L, 104.37 g/L, 11.13 g/L, with a magnesium to lithium ratio equivalent to 120.00 in an old brine in a salt lake located in Qaidam Basin of Qinghai province. 20 mL of the old brine in embodiment 1 was taken into a 100 mL beaker and the mass ratio of magnesium to lithium in the mixture was equal to 52.58. The brine was heated for condensation above a temperature adjustable furnace. Water was evaporated, which accounted for 30% of total mass of the brine, and the solution were changed into hydrated halide salts after cooling. The salts were transferred into a mechanical mixing vessel, and 18.33 mL of tributyl phosphate as well as 18.34 mL of 2-ethylhexanol were added to achieve a mass to volume ratio equivalent to 1:2 (g/mL). Solid-liquid extraction was carried out for 30 mins under room temperature. Then solid liquid mixtures were transferred in a sand core funnel and vacuum filtration was carried out, and the extracted organic-phase filtrate and remaining halide salts were obtained. The remaining halide salts were dissolved in water and fix its volume to 1000 mL in a volumetric flask. Samples were taken to analyze the concentration of $Li^+$ and $Mg^{2+}$ thereof. The results showed that a extraction rate of $Li^+$ was 55.5%; a extraction rate of $Mg^{2+}$ was 4.2% and a mass ratio of magnesium to lithium was 9.1 in the organic extracted phase.

The extracted phases from four stages were merged and organic extraction phase and water were respectively added in a separating funnel with a phase ratio of organic phase to water $V_o/V_w$ equivalent to 2:1 and reverse extraction was carried out. The mixtures were vibrated for 30 mins repeatedly in a temperature-constant cooling water bath SHA-2A at 20° C. and at a speed of 200 r/min. The solutions were then placed still for 30 mins and a reverse extracted water phase was finally obtained after phase separation, with a decreased magnesium to lithium ratio. Samples were analyzed and results showed that reverse extraction rate of $Li^+$ was up to 93.6%; reverse extraction rate of $Mg^{2+}$ was 88.2%; and a mass ratio magnesium to lithium declined to 8.5 in the reserve extracted water phase. In the concentrated reverse extracted solution with a low magnesium to lithium ratio, sodium carbonate solution was added to remove majority of $Mg^{2+}$, then sodium hydroxide was again added into the solution after separation, to completely precipitate magnesium. Solution of sodium carbonate was added into the filtered solution to form precipitation, and separation and desiccation were carried out to obtain a lithium carbonate product.

The above contents are only preferred embodiments of the present invention, and embodiments of present invention is not limited to this. The present invention have different kinds of modifications and changes for those skilled in the art. Any modification, equivalent replacement, improvement and the like made within spirits and principles of the present invention shall be included in the protection scope of the present invention.

What is claimed is:

1. A method for producing lithium carbonate from low-lithium brine by separating magnesium and enriching lithium, comprising:
   a. heating, evaporating and condensing a salt-lake brine to separate halide salts;
   b. extracting the separated halide salts with trialkyl phosphate or a mixture of trialkyl phosphate and monohydric alcohol as an organic phase;
   wherein a ratio of weight (kg) of the separated halide salts to a volume (L) of the organic phase is 1.0:0.5~5.0;
   c. filtering a mixture from step b to produce an organic phase and remaining halide salts after a two-phase separation;
   d. reverse extracting the organic phase from step c with water as a reverse extraction agent at a volume ratio of water to organic phase of 1.0:0.5~10.0 in 1-5 stages of reverse extraction;
   e. separating the organic phase from the water of step d after liquid layers are formed and then evaporating and concentrating the separated water to obtain a concentrated water phase;
   f. adding sodium carbonate or sodium hydroxide into the concentrated water phase from step e to precipitate magnesium carbonate or magnesium hydroxide, and then filtering the precipitated magnesium carbonate or magnesium hydroxide to remove $Mg^{2+}$, wherein the water phase has a pH of more than 10 to completely precipitate $Mg^{2+}$; and
   g. adding sodium carbonate into the water phase with $Mg^{2+}$ removed from step f to precipitate lithium carbonate, and then filtering and drying the precipitated lithium carbonate to produce a final product.

2. The method of claim 1, wherein step b comprises: first extracting the halide salts, and then heating and melting the remaining halide salts, wherein the water content of the remaining halide salts is controlled such that the halide salts containing crystal water are separated out; adding trialkyl phosphate or a mixture of trialkyl phosphate and monohydric alcohol to the halide salts containing crystal water at a volume-mass ratio of 1.0:0.5~5.0 to perform a second stage extraction.

3. The method of claim 1, wherein step b is multi-stage cross flow extraction or multi-stage counter flow extraction.

4. The method of claim 1, wherein trialkyl phosphate in step b is selected from the group consisting of: tributyl phosphate, tripentyl phosphate, trihexyl phosphate, tri-n-heptyl phosphate, trioctyl phosphate and isomerides thereof; the monohydric alcohol is selected from one or more of saturated monohydric alcohols having 6-20 carbon atoms; and a volume ratio of trialkyl phosphate to monohydric alcohol is 1.0:0.2~4.0.

5. The method of claim 1, wherein, when a mass ratio of magnesium to lithium is larger than 1.0 in the reverse extracted water phase from step e, steps a to e are repeated on the reverse extracted water phase from step e to further reduce a magnesium to lithium ratio.

* * * * *